United States Patent [19]
Schroeder et al.

[11] Patent Number: 5,965,792
[45] Date of Patent: Oct. 12, 1999

[54] NUCLEIC ACIDS ENCODING METAL UPTAKE TRANSPORTERS AND THEIR USES

[75] Inventors: Julian I. Schroeder, La Jolla, Calif.; Danuta M. Antosiewicz, Warsaw, Poland; Daniel P. Schachtman, Tranmere, Australia; Stephan Clemens, San Diego, Calif.

[73] Assignee: The Regents of the University of California, Oakland, Calif.

[21] Appl. No.: 08/900,148

[22] Filed: Jul. 28, 1997

Related U.S. Application Data

[60] Provisional application No. 60/022,722, Jul. 29, 1996.
[51] Int. Cl.[6] .......................... C12N 15/29; C12N 15/82; A01H 4/00; A01H 5/10
[52] U.S. Cl. ...................... 800/278; 435/419; 435/320.1; 435/418; 435/410; 435/69.1; 435/70.1; 435/468; 536/23.6; 536/23.1; 800/295
[58] Field of Search .................................. 435/69.1, 70.1, 435/468, 410, 419, 320.1, 418; 536/23.6, 23.1; 800/278, 295

[56] References Cited

PUBLICATIONS

Sentenac et al., *Science* 256:663–665 (1992).
Anderson et al., *Proc. Natl. Acad. Sci. USA* 89:3736–3740 (1992).
Ninnemann et al., *EMBO J.* 13:3464–3471 (1994).
Schachtman et al., *Science* 258:1654–1658 (1992).
Hoshi, *The J. of General Physiology* 105:309–328 (1995).
Bertl, *Folia Microbiologica* 39:507–509 (1994).
Huang et al., *Proc. Natl. Acad. Sci. USA* 91:3473–3477 (1994).
Armhein et al., "Molecular aspects of plant biochemistry." *Current Opinion in Biotechnology.* 6:159–164 (1995).
Schactman et al., "Structure and transport mechanism of a high–affinity potassium uptake transporter from higher plants." *Nature* 370:655–658 (1994).
Cao, et al., "Multiple genes, tissue specificity, and expression–dependent modulation contribute to the functional diversity of potassium channels in *arabidopsis thaliana*." *Plant Physiol.* 109:1093–1106 (1995).
Napoli et al. The Plant Cell. 1989. vol. 2: 278–289, 1989.
Tepperman et al. Plant Molecular Biology. 1990. vol. 14: 501–511. 1990.
Crane et al. Current Genetics. 1994. vol. 26: 443–450
Attached sequence, 1994.

*Primary Examiner*—Lynette R. F. Smith
*Assistant Examiner*—Ousama M-Faiz Zaghmout
*Attorney, Agent, or Firm*—Townsend and Townsend and Crew

[57] ABSTRACT

The invention provides LCT1 nucleic acids which encode metal ion uptake transporters. The invention also provides methods of modulating heavy metal and alkali metal uptake in plants. The methods involve producing transgenic plants comprising a recombinant expression cassette containing an LCT1 nucleic acid linked to a plant promoter.

29 Claims, No Drawings

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1982 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 137..1471
      (D) OTHER INFORMATION: /product= "low affinity cation
          transporter 1 (LCT1)"

(xi) SEQUENCE DESCRIPTION: SEQ ID NO:1:

```
AAGCTTGGTA CCGAGCTCGG ATCCACTAGT AACGGCCGCC AGTGTGGTGG AATTCAATTC      60

ATCTACGTTT CCACTCTCTT CCTCCTCTCC TCCTCGGACT GCTCAACGGT GGTCCGTCGT     120

CGGCGACGGC AGTTTG ATG ACG GCG CCG CCG CCT CCT CCT CTT CCT CCG        169
               Met Thr Ala Pro Pro Pro Pro Pro Leu Pro Pro
                 1               5                  10

ACT GCT CGG TGG TCC GTG GCC GGC CAC GGC AGT TTG ATG ACG GCA CCG      217
Thr Ala Arg Trp Ser Val Ala Gly His Gly Ser Leu Met Thr Ala Pro
             15                  20                  25

CCT CCT CCT CCT CCT CCT CCT GCT CGG TGG TCC GTG GCC GGC GAC GGC      265
Pro Pro Pro Pro Pro Pro Pro Ala Arg Trp Ser Val Ala Gly Asp Gly
         30                  35                  40

AGT TTG ATG ACG ACG CCG CCT CCT CCT CCT CCC ACT GCT CGG TGG TCC      313
Ser Leu Met Thr Thr Pro Pro Pro Pro Pro Pro Thr Ala Arg Trp Ser
     45                  50                  55

GTG GCC GGC GAC GGC AGT TTG ATG AAG GCG CCG CCT CCT CCT CCT CCT      361
Val Ala Gly Asp Gly Ser Leu Met Lys Ala Pro Pro Pro Pro Pro Pro
 60                  65                  70                  75

CCT CCT CCT CCG ACT GCT CGG TGG TCC GTG GCC GGC GGC GGC AGT TTG      409
Pro Pro Pro Pro Thr Ala Arg Trp Ser Val Ala Gly Gly Gly Ser Leu
                 80                  85                  90

ATG AGG GCT CCG CCG ATC CCA CTC TCT CGT GAA AGA CTC GCT CTA CCA      457
Met Arg Ala Pro Pro Ile Pro Leu Ser Arg Glu Arg Leu Ala Leu Pro
                 95                 100                 105

TAC CAG GAC GGT GAG CCA CCG GCC ACG ACC GAC GAC CTA AGC ATG AGG      505
Tyr Gln Asp Gly Glu Pro Pro Ala Thr Thr Asp Asp Leu Ser Met Arg
                110                 115                 120

CCG ACA TCC TCT CCG CCA CCA ACC AGC GCT GAA GAA ACA CAA GGA GCA      553
Pro Thr Ser Ser Pro Pro Pro Thr Ser Ala Glu Glu Thr Gln Gly Ala
        125                 130                 135

CGG CGT TCT TCC GTT TCG CCG GCA CCC GTC ACC ACG GGG ATG GCC ACC      601
Arg Arg Ser Ser Val Ser Pro Ala Pro Val Thr Thr Gly Met Ala Thr
140                 145                 150                 155

TCT CGC GGG CCG TCT ACC CTC ATC GAG GCC GAG GAG GGT CGT GCA ACT      649
Ser Arg Gly Pro Ser Thr Leu Ile Glu Ala Glu Glu Gly Arg Ala Thr
                160                 165                 170

GAG AGG AAG GAG ATT GTG GTG AAA TTG CTT AAA GCC AGG GCC AAG GAC      697
Glu Arg Lys Glu Ile Val Val Lys Leu Leu Lys Ala Arg Ala Lys Asp
                175                 180                 185

AAC CTC GAG CTC GGC GGC ATA GCC GCC ATC TTT GGT TTC GCT GTG CTG      745
Asn Leu Glu Leu Gly Gly Ile Ala Ala Ile Phe Gly Phe Ala Val Leu
                190                 195                 200

TTT GGT TGG TCC TGC TTC CCC GAG GAG ATG AAG CGC CCC GGC AAC TTG      793
Phe Gly Trp Ser Cys Phe Pro Glu Glu Met Lys Arg Pro Gly Asn Leu
    205                 210                 215

AAA TTC ATC TTC TCC TTG CTG CTG GCA ATC GCA ACC TTC TTC AGC GGC      841
Lys Phe Ile Phe Ser Leu Leu Leu Ala Ile Ala Thr Phe Phe Ser Gly
220                 225                 230                 235

ACG GCC CTC ACG CTC CTC AGC ATG AAC ATC GTC GGC CTG CCG GAG AGC      889
Thr Ala Leu Thr Leu Leu Ser Met Asn Ile Val Gly Leu Pro Glu Ser
                240                 245                 250

CTC GTC TCC GCC GGC CAG CTG GTC GCC TCC AAG TGC CTA TTT CTC ATC      937
Leu Val Ser Ala Gly Gln Leu Val Ala Ser Lys Cys Leu Phe Leu Ile
                255                 260                 265

TGC ACC GCG CTG TCC GCC ATG ACT CTG GTT AGT CTC CTG GCC CTC CTG      985
Cys Thr Ala Leu Ser Ala Met Thr Leu Val Ser Leu Leu Ala Leu Leu
                270                 275                 280
```

-continued

| | | |
|---|---|---|
| CCG AGC ATG CTC TAC CTG TGC CTT GGC CTC GTC GTG ATG ACG GTA GTC<br>Pro Ser Met Leu Tyr Leu Cys Leu Gly Leu Val Val Met Thr Val Val<br>285                            290                          295 | | 1033 |
| GTG CTG CCG GCC ATC GTG GTA CAC TGT TAC ATG CGA CGG CAC ACA GAG<br>Val Leu Pro Ala Ile Val Val His Cys Tyr Met Arg Arg His Thr Glu<br>300                          305                         310                      315 | | 1081 |
| GGA GGA GAC GAG GCA GCG GCA CTC GAG GAG CAT AAG GAG GAG CTG GAG<br>Gly Gly Asp Glu Ala Ala Ala Leu Glu Glu His Lys Glu Glu Leu Glu<br>                    320                          325                         330 | | 1129 |
| GCC GCA TCA AAG ATC ACC TCG TGC GTC ACC AAC TCG GCG TTC GGG GGA<br>Ala Ala Ser Lys Ile Thr Ser Cys Val Thr Asn Ser Ala Phe Gly Gly<br>                335                          340                        345 | | 1177 |
| CTG GTC GGT GTG CTG TTT AGC GCA TCC AAG TCC AAG GTC TCC GGC GCC<br>Leu Val Gly Val Leu Phe Ser Ala Ser Lys Ser Lys Val Ser Gly Ala<br>350                            355                         360 | | 1225 |
| CCG ACG GCC GTT TAC ACG GCT ATG TTT TTC ATG TTC TCC ACC GCC ATC<br>Pro Thr Ala Val Tyr Thr Ala Met Phe Phe Met Phe Ser Thr Ala Ile<br>     365                          370                         375 | | 1273 |
| TTC GGC ATG GTC GTC ATG ACA ATG TCG AAG AAA GTA TCG AAG GTC GCC<br>Phe Gly Met Val Val Met Thr Met Ser Lys Lys Val Ser Lys Val Ala<br>380                            385                         390                      395 | | 1321 |
| AAT CGG AGG CTC CGG CAG TTG CTC GTC TGG GCG ATC AGG CTC GCC AAC<br>Asn Arg Arg Leu Arg Gln Leu Leu Val Trp Ala Ile Arg Leu Ala Asn<br>                    400                          405                        410 | | 1369 |
| GCC TTT TTG CTC TGC TCG CTG GCG TGC GCA GCG TTC GCA GCA TCG TTC<br>Ala Phe Leu Leu Cys Ser Leu Ala Cys Ala Ala Phe Ala Ala Ser Phe<br>               415                          420                        425 | | 1417 |
| GCG GTC ATC AGA TGC CAA ATT TTT GCG GCG TTC GGC CGT TGG CCA TTA<br>Ala Val Ile Arg Cys Gln Ile Phe Ala Ala Phe Gly Arg Trp Pro Leu<br>          430                          435                        440 | | 1465 |
| CGG CTG TGATCTGTTT GATCCTCCAT CATTGTACTG TCCGCCCTGG CGAAGCCGAC<br>Arg Leu<br>     445 | | 1521 |
| CCGAGAAACC AGGAGAATCA AAAGGCCCGG CTCAAAGTAA TGGAGGACAT GGCGAGCAAG | | 1581 |
| GTGACGGCGG CGACGTTGGG GGCGATCATG AGCGTTCTCG CAGGCTCTGT CGGGGAGGAA | | 1641 |
| CACCACGAGA AGAAGGGGGC TACGGATGCA TTCATGGTTG TCCTGACATC GACCTTTGTC | | 1701 |
| TCAAGCTTTG GATTCATGCT TCTCGCCGCC GCGCCGAGCT CAGCGAGGGT GTACCTTGCA | | 1761 |
| CCGGTCTCCA AGGTGCTCAT CTGGTCGTCG GTGGCCTTGT TTGGAGCCAC CGCCGTCTCT | | 1821 |
| GTTTATAGCG CAGAGATCTC CAGGGCAGTT AGCCAGTAGT GTCCGTAATT TGTTGCTTGC | | 1881 |
| TTGAACTAAC TCAGTGGGTA GCCGTCGTAT ATTGTGATTG GATTGGTTGC TACTGCGAAT | | 1941 |
| GGCTGGATTT TTGCAATGAA AAAAAAAAAA AAAAAAAAA A | | 1982 |

(2) INFORMATION FOR SEQ ID NO:2:

(i) SEQUENCE CHARACTERISTICS:
        (A) LENGTH: 445 amino acids
        (B) TYPE: amino acid
        (D) TOPOLOGY: linear (ii) MOLECULE TYPE: protein (xi) SEQUENCE DESCRIPTION: SEQ ID NO:2:

Met Thr Ala Pro Pro Pro Pro Leu Pro Pro Thr Ala Arg Trp Ser
1                5                    10                  15

Val Ala Gly His Gly Ser Leu Met Thr Ala Pro Pro Pro Pro Pro
             20                    25                    30

Pro Pro Ala Arg Trp Ser Val Ala Gly Asp Gly Ser Leu Met Thr Thr
             35                    40                    45

```
Pro Pro Pro Pro Pro Thr Ala Arg Trp Ser Val Ala Gly Asp Gly
        50                  55                  60

Ser Leu Met Lys Ala Pro Pro Pro Pro Pro Pro Pro Pro Pro Thr
65                  70                  75                  80

Ala Arg Trp Ser Val Ala Gly Gly Ser Leu Met Arg Ala Pro Pro
                85                  90                  95

Ile Pro Leu Ser Arg Glu Arg Leu Ala Leu Pro Tyr Gln Asp Gly Glu
                100                 105                 110

Pro Pro Ala Thr Thr Asp Asp Leu Ser Met Arg Pro Thr Ser Ser Pro
                115                 120                 125

Pro Pro Thr Ser Ala Glu Glu Thr Gln Gly Ala Arg Arg Ser Ser Val
                130                 135                 140

Ser Pro Ala Pro Val Thr Thr Gly Met Ala Thr Ser Arg Gly Pro Ser
145                 150                 155                 160

Thr Leu Ile Glu Ala Glu Glu Gly Arg Ala Thr Glu Arg Lys Glu Ile
                165                 170                 175

Val Val Lys Leu Leu Lys Ala Arg Ala Lys Asp Asn Leu Glu Leu Gly
                180                 185                 190

Gly Ile Ala Ala Ile Phe Gly Phe Ala Val Leu Phe Gly Trp Ser Cys
                195                 200                 205

Phe Pro Glu Glu Met Lys Arg Pro Gly Asn Leu Lys Phe Ile Phe Ser
210                 215                 220

Leu Leu Leu Ala Ile Ala Thr Phe Phe Ser Gly Thr Ala Leu Thr Leu
225                 230                 235                 240

Leu Ser Met Asn Ile Val Gly Leu Pro Glu Ser Leu Val Ser Ala Gly
                245                 250                 255

Gln Leu Val Ala Ser Lys Cys Leu Phe Leu Ile Cys Thr Ala Leu Ser
                260                 265                 270

Ala Met Thr Leu Val Ser Leu Leu Ala Leu Leu Pro Ser Met Leu Tyr
                275                 280                 285

Leu Cys Leu Gly Leu Val Val Met Thr Val Val Val Leu Pro Ala Ile
                290                 295                 300

Val Val His Cys Tyr Met Arg Arg His Thr Glu Gly Gly Asp Glu Ala
305                 310                 315                 320

Ala Ala Leu Glu Glu His Lys Glu Glu Leu Glu Ala Ala Ser Lys Ile
                325                 330                 335

Thr Ser Cys Val Thr Asn Ser Ala Phe Gly Gly Leu Val Gly Val Leu
                340                 345                 350

Phe Ser Ala Ser Lys Ser Lys Val Ser Gly Ala Pro Thr Ala Val Tyr
                355                 360                 365

Thr Ala Met Phe Phe Met Phe Ser Thr Ala Ile Phe Gly Met Val Val
                370                 375                 380

Met Thr Met Ser Lys Val Ser Lys Val Ala Asn Arg Arg Leu Arg
385                 390                 395                 400

Gln Leu Leu Val Trp Ala Ile Arg Leu Ala Asn Ala Phe Leu Leu Cys
                405                 410                 415

Ser Leu Ala Cys Ala Ala Phe Ala Ala Ser Phe Ala Val Ile Arg Cys
                420                 425                 430

Gln Ile Phe Ala Ala Phe Gly Arg Trp Pro Leu Arg Leu
                435                 440                 445
```

(2) INFORMATION FOR SEQ ID NO:3:

(i) SEQUENCE CHARACTERISTICS:

-continued (A) LENGTH: 19 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:3:

ATGACGGCGC CGCCGCCTC                                                    19

(2) INFORMATION FOR SEQ ID NO:4:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:4:

CAGCCGTAAT GGCCAACG                                                     18

NUCLEIC ACIDS ENCODING METAL UPTAKE TRANSPORTERS AND THEIR USES

CROSS REFERENCE TO RELATED APPLICATIONS

This is a continuation in part of provisional application 60/022,722, filed Jul. 29, 1996, which is incorporated herein by reference.

FIELD OF THE INVENTION

The present invention is directed to plant genetic engineering. In particular, it relates to new methods for producing transgenic plants useful in, for example, bioremediation and metal toxicity.

BACKGROUND OF THE INVENTION

Heavy metals occur at various concentrations in different types of soils. In trace amounts certain heavy metals such as copper (Cu) and zinc (Zn) perform vital structural roles as cofactors in enzyme homeostasis. However, when in excess, these heavy metals as well as non-essential metals such as cadmium (Cd), mercury (Hg) and lead (Pb) are toxic. Many human disorders have been attributed to ingestion of heavy metals including an increased rate in cancer in response to Cd.

Remediation of soils containing high levels of heavy metals requires physical removal of the metals, because most of these metals cannot be degraded in the soil, as is the case for certain organic contaminants. Current practical methods used to decontaminate such sites involve physical excavation of top soils, transport and reburial elsewhere. These clean-up methods are only feasible for small areas and are very costly. For example, cleaning one hectare to a depth of one meter can cost between $600,000 and $3,000,000.

Studies have shown that several plant types are effective at taking up significant concentrations of heavy metals from soils and waters (Baker & Brooks, *Biorecovery* 1: 81–126 (1989) and Dushenkov et al., *Environ. Sci. & Tech.* 29: 1239–1245 (1995)). These heavy metal "hyperaccumulators" are widespread throughout the plant kingdom. Most metal hyper-accumulating plants have been identified by selecting plants that grow on sites with high metal concentrations (e.g. mining sites). Some of the very efficient heavy metal hyper-accumulators such as *Thlaspi caerulescens* (Brown, *Environ. Soil & Tech.* 29: 1581–1858 (1995)) are relatively small or have small root systems and low biomass which limits their ability for removal and storage of large amounts of heavy metals. *Brassica juncea* plants, which produce larger biomass have been identified as efficient metal hyper-accumulators (Salt et al. *Plant Physiol.* 109: 1427–1433 (1995).

Initial studies indicate that removal of heavy metals from soils by plants would be orders of magnitude less costly and could become efficient by maximizing metal uptake through biological engineering (Cunningham & Ow et al., *Plant Physiol.* 110: 715–719 (1996); Brown et al., *J. Env. Qual.* 23: 1151–1157 (1994); and Salt et al., *Plant Phys.* 109: 1427–1433 (1995)). Several rate-limiting steps are critical for effective removal of heavy metals from soils. These include making the contaminants biologically accessible in the soil (by chelation and acidification) and subsequent uptake of heavy metals across the plasma membrane of root cells. Furthermore, upon entering plant cells, intracellular detoxification is achieved by production of appropriate high-affinity ligands or chelation proteins and peptides.

Several mechanisms of intracellular detoxification/chelation have been identified in plants including metallothionins (Hamer, *Annu. Rev. Biochem.* 55: 913–951 (1986) and Maitani, et al. *Plant Physiol.* 110: 1145–1150 (1996)), glutathione-derived phytochelatins (Howden et al. *Plant Physiol.* 107: 1059–1066 (1995) and Grill et al. *Science* 230: 674–676 (1985)), or metal binding amino acids (Kraemer et al. *Nature* 379: 635–638 (1996)).

A recent study has shown that reduction of the heavy metal Hg to its non-charged metallic form, which is less toxic, significantly reduces plant toxicity and can enhance removal of Hg (Rugh et al. *Proc. Nail. Acad. Sci. USA* 93: 3182–3187 (1996)). In a following detoxification step, heavy metal-peptide complexes are shuttled into the plant lysosomal vacuolar organelles (Ortiz et al. *EMBO J.* 11: 3491–3499 (1992) and Ortiz et al. *J. Biol. Chem.* 270: 4721–4728 (1995)). An ATP binding cassette (ABC)-type transporter has been shown to mediate vacuolar sequestration of heavy metals in yeast. Sequestration of conjugated heavy metal-peptide complexes in the large plant vacuoles effectively removes these compounds from various metal-sensitive enzymes in the plant cell cytoplasm (Salt et al. *Plant Phys.* 107: 1293–1301 (1995)). In addition, it is considered advantageous if heavy metals are further transported into shoots and leaves of plants before being sequestered into vacuoles as these aerial parts of the plant are more amenable to harvesting for heavy metal removal (Cunningham et al. *Plant Physiol.* 110: 715–719 (1996)). Identification of transporters that load heavy metals into the vascular tissue in roots and that enable heavy metal uptake into leaf cells from the vascular system will be essential for biological engineering of root to shoot transfer.

Plant plasma membrane cation uptake transporters have been isolated by complementation of yeast mutants deficient in accumulation of specific cationic nutrients (Sentenac et al. *Science* 256: 663–665 (1992); Anderson et al. *Proc. Natl. Acad. Sci. USA* 89: 3736–3740 (1992); Ninnemann et al. *EMBO J.* 13: 3464–3471 (1994); and Schachtman and Schroeder, *Nature* 370: 655–658 (1994)). Complementation of $K^+$ uptake deficient yeast mutants led to isolation of first $K^+$ channel cDNAs in plants, named AKT1 and KAT1 (Sentenac et al. and Anderson et al. supra). In voltage clamp experiments these two cDNAs were shown to encode inward-rectifying $K^+$ channels that provide a pathway for proton-driven low-affinity $K^+$ uptake (Schachtman, et al. *Science* 258: 1654–1658 (1992); Hoshi, *The Journal of General Physiology* 105: 309–328 (1995); Bertl, *Folia Microbiologica* 39: 507–509 (1994)).

Despite these advances, genes encoding heavy metal transporters in the plasma membranes of plant cells have not yet been isolated. Identification of genes encoding transporters that load heavy metals into the vascular tissue in roots and that enable heavy metal uptake into leaf cells from the vascular system will be essential for biological engineering of root to shoot transfer. The present invention addresses these and other needs.

SUMMARY OF THE INVENTION

The present invention provides isolated nucleic acids comprising a polynucleotide sequence which encodes an LCT1 polypeptide and hybridizes to SEQ ID NO: 1 under stringent conditions. The nucleic acids of the invention can be a wheat LCT1 gene as shown in SEQ ID NO: 1. If expression of the gene in transgenic plants or other organisms is desired the nucleic acids of the invention may further comprise a promoter operably linked to the polynucleotide sequence.

The invention also provides transgenic plants comprising a recombinant expression cassette comprising a plant promoter operably linked to a polynucleotide sequence which hybridizes to SEQ ID NO: 1 under stringent conditions. Other organisms such as yeast may also be used.

Definitions

The phrase "nucleic acid sequence" refers to a single or double-stranded polymer of deoxyribonucleotide or ribonucleotide bases read from the 5' to the 3' end. It includes self-replicating plasmids, infectious polymers of DNA or RNA and non-functional DNA or RNA.

As used herein, a "heavy metal" is a metal of specific gravity greater than 4, located in the lower half of the periodic table. Examples include cadmium, lead, zinc. antimony, mercury, silver, tin, copper, cesium, strontium, radium, uranium, osmium, beryllium, and aluminum.

The term "promoter" refers to a region or sequence determinants located upstream or downstream from the start of transcription and which are involved in recognition and binding of RNA polymerase and other proteins to initiate transcription. A "plant promoter" is a promoter capable of initiating transcription in plant cells.

The term "plant" includes whole plants, plant organs (e.g., leaves, stems, flowers, roots, etc.), seeds and plant cells and progeny of same. The class of plants which can be used in the method of the invention includes algae and higher plants amenable to transformation techniques. Higher plants useful in the invention include angiosperms (monocotyledonous and dicotyledonous plants), as well as gymnosperms. It includes plants of a variety of ploidy levels, including polyploid, diploid and haploid.

A "heterologous sequence" is one that originates from a foreign species, or, if from the same species, is substantially modified from its original form. For example, a heterologous promoter operably linked to a structural gene is from a species different from that from which the structural gene was derived, or, if from the same species, is substantially modified from its original form.

An "LCT1 nucleic acid" or "LCT1 polynucleotide sequence" (referred to as PMT1 nucleic acids in the parent application) of the invention is a subsequence or full length polynucleotide sequence of a gene which, when present in a transgenic plant, can be used to enhance heavy metal uptake and which hybridizes to SEQ ID NO: 1 under stringent conditions. An exemplary nucleic acid of the invention is the wheat LCT1 sequence in SEQ ID NO: 1. An LCT1 polynucleotide typically comprises or consists of a coding region of at least about 30–40 nucleotides to about 2200 nucleotides in length. Usually the nuclei acids are from about 100 to about 2000 nucleotides, often from about 500 to about 1500 nucleotides in length. The polypeptides encoded by the polynucleotides of the invention are a new class of metal transporter proteins. One of skill will recognize that in light of the present disclosure various modifications (e.g., substitutions, additions, and deletions) can be made to the polypeptide sequences without substantially affecting their function. These variations are specifically covered by the terms LCT1 polypeptide.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by the term LCT1 nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the term "LCT1 nucleic acid". In addition, the term specifically includes those full length sequences substantially identical (determined as described below) with an LCT1 polynucleotide sequence and that encode proteins that retain the function of the LCT1 polypeptide (e.g., resulting from conservative substitutions of amino acids in the LCT1 polypeptide).

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48: 443 (1970), by the search for similarity method of Pearson and Lipman *Proc. Natl. Acad. Sci.(U.S.A.)* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90% and most preferably at least 95 %, compared to a reference sequence using the programs described above (preferably BLAST) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfmethionine. Preferrehains is cysteine and methionine. Preferred conservative amino acids substitution groups are: valine-leucine-isoleucine, phenylalanine-tyrosine, lysine-arginine, alanine-valine, and aspsragine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

In the present invention, genomic DNA or cDNA comprising LCT1 nucleic acids of the invention can be identified in standard Southern blots under stringent conditions using the cDNA sequence shown in SEQ ID NO: 1. For the purposes of this disclosure, stringent conditions for such hybridizations are those which include at least one wash in 0.2× SSC at a temperature of at least about 50° C., usually about 55° C to about 60° C., for 20 minutes, or equivalent conditions.

DESCRIPTION OF THE PREFERRED EMBODIMENTS

This invention relates to plant LCT1 genes, such as the LCT1 genes of wheat. The invention provides molecular strategies for modulating heavy metal or alkali metal uptake in plants using LCT1 overexpression and antisense gene constructs. As explained below, the transport of alkali metals (including Li, Na, K, Rb, and Cs) can also be modulated. In addition, mutant forms of the gene can be prepared and used to modulate uptake by, for instance, increasing affinity for desired metals.

Two general pathways have been proposed for heavy metal accumulation across the plasma membrane of plant cells, both of which likely contribute in parallel to heavy metal uptake: (I) Metals may be chelated in soils and vascular tissue and the metal-chelate complexes could be taken up into plant cells. (II) Cation uptake transporters for physiological metals such as calcium (Ca2+) have been proposed to provide major pathways for heavy metal accumulation in plant roots (see, e.g., Huang et al. *Proc. Natl. Acad. Sci. USA* 91: 3473–3477 (1994) and Reid et al. *Planta* 198: 39–45 (1996)).

Metals such as Ca2+, Mg2+ and Fe3+ are plant nutrients and uptake of these metals is crucial for plant growth. Transporters for these plant nutrients have been proposed to represent the pathways for heavy metal uptake. Calcium channels and transporters provide a pathway for uptake of the nutrient Ca2+ and have been proposed to allow uptake of heavy metals such as Cd2+ (see, e.g., Huang et al., supra). Detailed studies on Zn uptake suggest that more than one pathway for uptake exists including low- and high-affinity mechanisms (Chaudry et al. *J. Exp. Bot.* 23: 552–560 (1972) and Kochian, in *Zinc in Soils and Plants*. (eds. Robson, A. D.) 45–57 (Kluwer, Boston, London, 1993)). It is likely that both Ca2+ transporters and Fe3+ transporters contribute to uptake of different heavy metals. Other studies in animal cells have shown that heavy metals such as Cd2+ bind strongly to calcium channels with affinities up to 690-fold greater than Ca2+ itself (Ellinor et al. *Neuron* 15: 1121–1132 (1995)). Furthermore, the voltage-dependent Ca2+ channels described to date in plants are less selective among divalent metals than their animal cell counterparts allowing significant Mg2+ influx currents (Thuleau et al., *EMBO J.* 13, 2970–2975 (1994) and Marshall et al., *Plant J.* 5: 683–694 (1994)).

Resting potentials in plant cells are in the range from −120 to −200 mV because of the activity of electrogenic proton-extruding ATPases (Sussman et al. *Annu. Rev. Plant Physiol.* 45: 211–234 (1994)). Assuming passive uptake of divalent heavy metals such as Cd2+ and Zn2+ via ion channels, membrane potentials of −120 to −200 mV will allow a $10^4$ to $4.6 \cdot 10^6$-fold accumulation of heavy metals inside root cells with respect to the soil (−30 mV per 10-fold cytosolic concentration of divalent heavy metals). Therefore a physiological transporter or cation channel for divalent nutrients such as Ca2+ and Mg2+ should provide a significant pathway for uptake and accumulation of heavy metals in plant cells. Indeed, metal hyper-accumulating plants are known to be able to accumulate metals up to 3% of leaf dry weight (Baker et al. *Biorecovery* 1: 81–126 (1989)).

As explained in detail below, using complementation cloning and screening for $Cd^{2+}$ sensitivity in yeast, novel plant root cDNAs that enhance metal uptake and increases $Cd^{2+}$ toxicity in yeast has been identified. One of the isolated cDNAs, named LCT1 (Low affinity Cation Transporter) was isolated by the ability to mediate metal uptake into yeast. Furthermore, Cd sensitivity screens in this heterologous system showed that LCT1 also enhances the sensitivity of yeast growth to extracellular Cd and Pb.

The LCT1 cDNA encodes a protein with approximately 6–8 hydrophobic domains suggesting that it encodes a membrane protein (see, SEQ ID NO:2). The finding that expression of LCT1 in yeast enhances Cd toxicity indicate that LCT1 mediates uptake of these toxic metals. The data presented here suggest that LCT1 encodes a first heavy metal plasma membrane uptake transporter cDNA isolated from higher plant cells. The nucleic acids of the invention can thus be used to modulate heavy metal uptake across the plasma membrane into higher plant cells.

Isolation of LCT1 Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989).

The isolation of LCT1 nucleic acids may be accomplished by a number of techniques. For instance, degenerate oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as roots, and a cDNA library which contains the LCT1 gene transcript is prepared from the mRNA. Alternatively, cDNA may be prepared from mRNA extracted from other tissues in which LCT1 genes or homologs are expressed.

The cDNA or genomic library can then be screened using a probe based upon the sequence of a cloned LCT1 gene disclosed here. Probes may be used to hybridize with genomic DNA or cDNA sequences to isolate homologous genes in the same or different plant species.

To identify nucleic acids of the invention, plants can be grown under conditions of heavy metal stress and under cationic nutrient starvation conditions. Messenger RNA isolation and Northern hybridization can be used to determine whether a) growth conditions affect expression levels of the genes of the invention and b) whether hyper-accumulators (e.g., *Thlaspi caerulescens* and *Brassica juncea*) constitutively show higher levels of LCT1 message when compared to non-hyper-accumulating relatives.

Alternatively, the nucleic acids of interest can be amplified from nucleic acid samples using amplification techniques. For instance, polymerase chain reaction (PCR) technology to amplify the sequences of the LCT1 genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying LCT1 sequences from plant tissues are generated from the sequences provided here. Particular primers conveniently used for this purpose are as follows:

atgacggcgccgccgcctc (SEQ ID NO:3)
cagccgtaatggccaacg (SEQ ID NO:4).

For a general overview of PCR see *PCR Protocols: A Guide to Methods and Applications*. (Innis, M, Gelfand, D., Sninsky, J. and White, T., eds.), Academic Press, San Diego (1990).

Polynucleotides may also be synthesized by well-known techniques as described in the technical literature. See, e.g., Carruthers et al., *Cold Spring Harbor Symp. Quant. Biol.* 47: 411–418 (1982), and Adams et al., *J. Am. Chem. Soc.* 105: 661 (1983). Double stranded DNA fragments may then be obtained either by synthesizing the complementary strand and annealing the strands together under appropriate conditions, or by adding the complementary strand using DNA polymerase with an appropriate primer sequence.

Use of Nucleic Acids of the Invention to Enhance LCT1 Gene Expression

The isolated sequences prepared as described herein, can be used in a number of techniques, for example, to introduce LCT1 gene expression into plant lacking the gene or to enhance endogenous expression. A particularly useful gene for this purpose is the LCT1 gene shown in SEQ ID NO: 1.

Isolated sequences prepared as described herein can be used to introduce expression of a particular. LCT1 nucleic acid to enhance or increase endogenous gene expression. Enhanced expression will lead to increased metal uptake.

Thus, plants comprising these constructs are particularly useful for removing heavy metals from contaminated soils. Where overexpression of a gene is desired, the desired gene from a different species may be used to decrease potential sense suppression effects. One of skill will recognize that the polypeptides encoded by the genes of the invention, like other proteins, have different domains which perform different functions. Thus, the gene sequences need not be full length, so long as the desired functional domain of the protein is expressed.

Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain. Such modifications are particularly useful for preparation of transporters with increased affinity for the desired metal ion. Such transporters can then be used in bioremediation.

Expression of plant metal uptake transporters in yeast provides a convenient means to identify mutations involved in metal selectivity of individual transporters. For example, identification of mutations in specificity and other properties of the transporters of the invention can be carried out as described by Anderson et al. *Soc. Exp. Biol Symp.* 48:85–97 (1994); Uozumi et al. *J. Biol. Chem.* 270: 24276–24281 (1995) and Rubio et al. *Science* 270: 1660–1663 (1995)). For example, LCT1 mutants can be identified which either enhance uptake of heavy metals and alkali metals for bioremediation or alternatively mutants can be generated which more specifically take up particular nutrients while excluding toxic metals such as $Cd^{2+}$, $Na^{+.}$ The effects of mutations and/or altered expression of the nucleic acids of the invention can also be tested in plants. For these experiments uptake in intact, air-bubbled, roots is analyzed. The depletion of metals such as Ca2+, Pb2+ or Cd2+ from dilute minimal uptake buffers or the uptake of metals not present in plants, such as Pb2+ or Cd2+, by plant tissue can be conveniently measured by radioisotopic studies or atomic absorption spectrophotometry as described by Benlloch et al. *Plant Physiol.* 90: 939–942 (1989). In brief, for depletion experiments, the plant tissue is placed in a minimal solution containing the desired concentrations of ions, and aliquots are removed at intervals of 1 to 5 min. After the depletion experiment, the plant tissue is carefully blotted and weighed to determine the fresh weight. The ionic concentrations of the removed aliquots are then measured by atomic absorption spectrophotometry, and the removal of ions by the plant tissue over time is calculated. The resolution of depletion experiments can be optimized by adjusting the weight of the plant tissue or the volume of the uptake solution. In Rb+ depletion experiments for example, uptake rates in the order of 0.5 to 4 $\mu$mol per g freshweight could be clearly resolved using approximately 0.5 g root tissue placed in 200 ml uptake solution containing 10 $\mu$M Rb+.

To measure uptake of ions, the intact plant roots are placed in the air-bubbled uptake solution for 1 to 15 min., removed, and placed in an unlabeled ice-cold rinse solution for 5 min. Binding of heavy metals or Ca2+ to cell walls can cause problems in determining uptake into root systems because of the high-affinity of cell wall binding sites for divalent cations. In order to minimize the effect of cell wall binding, the rinse solution contains 0.1 mM Mg2+, pH 5 and 20–100 mM Ca2+ to compete off most binding of other metals to cell walls. The plant tissue is then weighed as above and frozen. For extraction of metals, the tissue is thawed and soaked in 10% acetic acid for 12 h, and then washed with boiling water. The ionic concentrations of the combined liquids (10% acetic acid+ water) is determined by atomic absorption spectrophotometry, and the uptake of ions by the plant tissue is calculated.

As noted above, hyper-accumulating plants often have small root systems. Thus, it is often desirable to increase the biomass, particularly of roots in the plants of the invention. Plant transformation with *Agrobacterium rhizogenes* vectors or with plant cyclin-dependent protein kinases provide approaches to increase root size (Doerner et al. *Nature* 380: 520–523 (1996)).

Suppression of LCT1 Expression

The sequences of the invention can also be used to inhibit expression of an endogenous gene and thereby decrease metal uptake or to replace the wild type gene, which can then be replaced with a mutant transgene with desired characteristics. A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA,* 85: 8805–8809 (1988), and Hiatt et al., U.S. Pat. No. 4,801,340.

The nucleic acid segment to be introduced generally will be substantially identical to at least a portion of the endogenous LCT1 gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 1700 nucleotides is especially preferred.

Catalytic RNA molecules or ribozymes can also be used to inhibit expression of LCT1 genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature,* 334: 585–591 (1988).

Another method of suppression is sense suppression. Introduction of nucleic acid configured in the sense orientation has been recently shown to be an effective means by which to block the transcription of target genes. For an example of the use of this method to modulate expression of endogenous genes see, Napoli et al., *The Plant Cell* 2: 279–289 (1990), and U.S. Pat. Nos. 5,034,323, 5,231,020, and 5,283,184.

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Other methods for altering or replacing genes are known in the art. For instance, insertional mutants using T-DNA or transposons can be generated. See, e.g., Haring, et al., *Plant Mol. Biol.* 16: 449–469 (1991) and Walbot, *Ann. Rev. Plant Mol. Biol.* 43: 49–82 (1992). Another strategy in genetic engineering of plants and animals is targeted gene replacement. Homologous recombination has typically been used for this purpose (see, Capecchi, *Science* 244: 1288–1292 (1989)).

Production of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22: 421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium tumafaciens*, and other transcription initiation regions from various plant genes known to those of skill.

Alternatively, the plant promoter may direct expression of the LCT1 nucleic acid in a specific tissue or may be otherwise under more precise environmental or developmental control. Such promoters are referred to here as "inducible" or "tissue-specific"promoters, respectively. Examples of environmental conditions that may effect transcription by inducible promoters include anaerobic conditions, elevated temperature, or the presence of light.

Examples of promoters under developmental control include promoters that initiate transcription predominantly in certain tissues, such as roots, fruits, seeds, flowers, and the like. Root-specific promoters are typically used in the present invention. Examples of root-specific include the promoter from the alcohol dehydrogenase gene (DeLisle et al. *Int. Rev. Cytol.* 123, 39–60 (1990)).

Uptake of heavy metals into other tissues, in addition to roots, is important for heavy metal removal. In particular transport of heavy metals into shoot and leaf cells is essential for facilitating harvesting of plants that hyper-accumulate heavy metals. Therefore targeted expression of LCT1 to cell layers surrounding the vascular system which is responsible for transporting heavy metals from roots to leaves is useful in enhancing uptake of heavy metals from the vascular tissue into leaves and surrounding shoot cells. For enhanced heavy metal uptake across the plasma membrane of leaf cells, highly tissue-specific CAB promoters (Bansal, *Proc. Natl. Acad. Sci. USA* 89: 3654–3658 (1992)) or the HKT1 promoter can be used (Schachtman and Schroeder *Nature* 370: 655–658 (1994)).

If proper polypeptide expression is desired, a polyadenylation region at the 3'-end of the coding region should be included. The polyadenylation region can be derived from the natural gene, from a variety of other plant genes, or from T-DNA.

The vector comprising the sequences from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *EMBO J.* 3: 2717–2722 (1984). Electroporation techniques are described in Fromm et al. *Proc. Natl. Acad. Sci. USA* 82: 5824–(1985). Ballistic transformation techniques are described in Klein et al. *Nature* 327: 70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233: 496–498 (1984), and Fraley et al. *Proc. Natl. Acad. Sci. USA* 80: 4803 (1983).

Transformed plant cells which are derived by any of the above transformation techniques can be cultured to regenerate a whole plant which possesses the transformed genotype and thus the desired phenotype such as increased heavy metal uptake. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38: 467–486 (1987).

The nucleic acids of the invention can be used to confer desired traits on essentially any plant. Thus, the invention has use over a broad range of plants, including species from the genera Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanurn, Sorghum, Trigonella, Triticum, Vitis, Vigna, and, Zea.

Incorporation of the genes of the invention into plants useful in bioremediation is a preferred embodiment. Suitable plants for this purpose include those known to be hyperaccumulators of heavy metals. Examples include *Brassica juncea* and *Thlaspi caerulescens* and large plants with great biomass that have been engineered to with stand increased metal uptake by enhancing metal sequestration, chelation and/or vacuolar uptake.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Expression in Other Organisms

The LCT1 polypeptides may also be expressed in recombinantly engineered cells such as bacteria, yeast or other fungi. It is expected that those of skill in the art are knowledgeable in the numerous expression systems available for expression in these systems. No attempt to describe in detail the various methods known for the expression of proteins in prokaryotes or eukaryotes will be made.

EXAMPLE

The following Example is offered by way of illustration, not limitation.

I. Cloning of LCT1, a Metal Uptake Transporter

By complementation of cation uptake yeast mutants with a size-selected wheat root cDNA library we have isolated a cDNA, LCT1, with a novel primary structure. Initial studies show that the cDNA allows uptake of the radio-isotopic alkali-metals $Na^+$ and $Rb^+$. The rate of alkali metal uptake via this transporter as a function of cation concentration shows that LCT1 mediates low-affinity transport of alkali metals.

Northern blot analysis shows higher LCT1 expression levels in roots than in leaves of wheat. LCT1 encodes a polypeptide with a predicted molecular mass of about 60 KDa. Hydrophobicity analysis of the deduced amino acid sequence shows that the protein encodes a hydrophobic polypeptide comprising approximately 6–8 putative transmembrane spans, consistent with a role as a plasma membrane transporter. The protein sequence shows no significant homology to other known genes. Only in small non-hydrophobic domains, weak (perhaps insignificant) homologies to other proteins were found. Taken together these data indicate that LCT1 encodes a novel type of metal uptake transporter in higher plant roots.

Secondary yeast screens were pursued to identify plant root cDNAs that render yeast growth sensitive to heavy metals. These screens represent a negative selection of (non-growing) colonies in the presence of low levels of Cd and therefore replica-plating techniques were used for colony selection (Sherman, F. *Meth. Enzymol.* 194: 3–21 (1991)). Using this approach, the same LCT1 cDNA described above was isolated by its ability to confer $Cd^{2+}$ toxicity to yeast growth. Control experiments including re-isolation of the LCT1 carrying plasmid and re-transformation of yeast, as well as growth curves measured in liquid cultures in the presence of Cd confirm that expression of LCT1 in yeast increases $Cd^{2+}$ toxicity when compared to vector-transformed control yeast lines.

Additional experiments were conducted to determine whether LCT1 expression induces lead (Pb) sensitivity upon yeast growth. These experiments are more complex than Cd experiments because of the high reactivity of Pb with various nutrients in yeast growth media leading to both lead chelation and precipitation. Phosphate-free nutrient media were used by replacing phosphate with phosphoserine to reduce lead precipitation. Using the program GEOCHEM (Parker, D. R., Nervell, W. A. & Chaney, R. L. in *Soil Chemical Equilibrium and Reaction Models*. (eds. Loeppert, R.) (American Society of Agronomy, Soil Science Society of America, Madison, Wis., 1994)), approximate concentrations of different Pb complexes were calculated. Pb sensitivity experiments were performed in liquid cultures and showed that growth of LCT1-expressing yeast was more sensitive to Pb than controls. However, in contrast to Cd-toxicity at 1 $\mu$M added Cd, larger added Pb concentrations were required to generate enhanced toxicity in LCT1-expressing yeast when compared to the non-LCT1 expressing control line.

Pb sensitivity experiments in liquid yeast growth media are only of semi-quantitative nature because of Pb reactivity, large effects of minor pH changes and formation of many complexes according to GEOCHEM analysis. Therefore further direct experiments were undertaken, by measuring Pb uptake in minimal non-precipitating/chelating media (described below).

II. LCT1 Mediates Uptake of Cd and Pb

A number of different mechanisms could be responsible for enhanced sensitivity of LCT1-expressing yeast growth towards heavy metals. For example, nutrient uptake into yeast may be blocked by heavy metals without the heavy metals actually being taken up. To determine whether LCT1 influences uptake of Cd and Pb, direct measurements of uptake of these heavy metals were performed. Two independent methods for measuring metal uptake into yeast were pursued: High-resolution atomic absorption spectroscopy using a heated graphite furnace and uptake of radioactively labeled metals ($^{109}Cd$ & $^{45}Ca^{2+}$). Both methods are described in the art (see, Schachtman, & Schroeder, *Nature* 370: 655–658 (1994) and Rubio et al., *Science* 270: 1660–1663 (1995)).

Extracellular binding of $Cd^{2+}$ to cell walls can account for apparent uptake in uptake measurements. Therefore, all uptake experiments were performed after washing cells 3 times in the presence of high 20 to 100 mM $Ca^{2+}$ concentrations and at an acid pH (4.5) which should effectively out-compete $Cd^{2+}$ binding to cell walls. Control experiments, in which yeast cells were transformed with the empty yeast expression vector (PYES2, Invitrogen), showed that low background $Cd^{2+}$ accumulation occurred in yeast, as expected. The $Cd^{2+}$ toxicity associated with LCT1 expression suggests that the heavy metal may be taken up into the cytoplasm. When the LCT1 cDNA was expressed in yeast, Cd uptake was strongly enhanced. Both atomic absorption studies and uptake studies with radioactively labeled $^{109}Cd^{2+}$ showed that LCT1 expression in yeast greatly enhances Cd uptake.

Further experiments were performed to determine whether LCT1 also affects Pb uptake into yeast. For these experiments, as well as for the above described Cd uptake experiments, short term uptake rates were measured in minimal salt solutions which reduce Pb chelation (0.1 mM $MgCl_2$, 1 mM $CaOH+CaCl_2$, 2% sucrose, 5 mM MES, pH 6.0). Cells pre-grown in growth medium were washed 3 times before suspension in the minimal uptake buffer. In vector-transformed control experiments without LCT1 expression, a low rate of Pb uptake into yeast was found when yeast cells were exposed to 1 $\mu$M Pb. Expression of LCT1 in yeast produced a significant enhancement in Pb uptake.

III. LCT1 Enhances $Ca^{2+}$ Uptake

Studies have suggested that physiological nutrient uptake transporters for divalent and trivalent metals such as $Ca^{2+}$, $Mg^{2+}$ & Fe may provide molecular pathways for heavy metal uptake across the plasma membrane of plant cells (Huang et al., *Proc. Natl. Acad. Sci. USA* 91, 3473–3477 (1994)). The hydrophobic structure, the sensitivities of yeast growth towards Cd and Pb, as well as the enhancement of Cd and Pb uptake in LCT1-expressing yeast suggest that LCT1 may function as a cation uptake transporter. Therefore, further experiments were performed to determine whether LCT1 enhances $Ca^{2+}$ uptake. Uni-directional $Ca^{2+}$ influx was measured in yeast using the radioisotope $^{45}Ca^{2+}$. In control, vector-transformed yeast cells background levels of $^{45}Ca^{2+}$ uptake were measured at 1 mM total external $Ca^{2+}$. Expression of LCT1 in yeast led to a significant enhancement in $^{45}Ca^{2+}$ uptake. These studies showed that LCT1 expression in yeast enhances $^{45}Ca^{2+}$ uptake.

The results discussed above together suggest that LCT1 likely encodes a first plant membrane transporter that facilitates heavy metal and alkali metal uptake. The hypothesis that LCT1 functions as a transporter was further tested in initial competition experiments. If LCT1 is able to transport $Cd^{2+}$, Pb and $Ca^{2+}$, it can be assumed that competition for uptake of these metals would occur. In further studies we found that increasing the extracellular $Ca^{2+}$ concentration to higher millimolar levels, reduces the Cd toxicity of LCT1-expressing yeast. These preliminary experiments suggest competition among metals supporting a role for LCT1 in metal uptake. We note however, that in spite of this Cadmium-Calcium competition, Cd and Pb uptake into yeast are enhanced by LCT1 even when Cd or Pb concentrations are 100-fold lower than the concentration of the nutrient $Ca^{2+}$. Since these metal concentrations are within the ranges found in soils, this finding is significant. It is interesting that for $Ca^{2+}$ channels in animal cells, in the presence of alkali metals, the $K_{1/2}$ for Cd binding ($K_{1/2}$=1.4 nM) has been recently shown to be about 690-fold tighter than binding of the physiological metal $Ca^{2+}$ ($K_{1/2}$=970 nM).

IV. LCT1 Can Mediate Cadmium Removal

Further experiments were pursued to determine whether LCT1 expression in yeast allows removal of cadmium from the growth medium. In these experiments Cd removal was assayed by measuring residual cadmium levels at different times in the growth medium using atomic absorption spectroscopy after subtracting background removal and cell wall binding levels found in control vector-transformed yeast. When yeast were incubated in growth media including 10 $\mu$M cadmium, an enhancement in the rate of reduction in the growth medium concentration of cadmium was observed in LCT1-expressing yeast when compared to vector-transformed controls.

V. Genetic Screening for LCT1 Mutants

The finding that LCT1 expression increases the Cd sensitivity of yeast growth can be utilized to attempt isolation of mutations in LCT1 that either enhance or reduce Cd uptake. Isolation of mutations that alter the interaction of LCT1 with toxic metals would be of interest for two reasons: (A) mutations within various domains of LCT1 (e.g., hydrophobic domains) can be used to change the metal specificity of LCT1-mediated uptake. (B) Using genetic selection it may be possible to isolate mutants in LCT1 that allow enhanced uptake of heavy metals while reducing uptake of other metals.

Hydroxylamine mutagenesis produces point mutations in plasmid DNA (Sikorski, et al., *Meth. Enzymol.* 194: 319–329 (1991)). In an initial attempt, a plasmid library of ~10,000 hydroxylamine-mutagenized LCT1 plasmids was generated. Putative mutants which confer Cd resistance could be isolated by transforming yeast and plating yeast on growth media containing $Cd^{2+}$. In an initial screen 1 putative full length Cd resistant mutant plasmid (Cdr1) was isolated. Note that the Cdr phenotype could result from a non-functional LCT1 mutant. Therefore, with the goal of identifying LCT1 mutations that enhance cadmium uptake, initial negative screens were pursued. In these negative screens, colonies are isolated that do not grow on 5 $\mu$M Cd using replica plating. Using this approach, after 4 successive rounds of screening to remove "false positive" colonies, 3 initial putative mutants were isolated that enhance Cd sensitivity (Cds1-3). At 10 $\mu$M Cd, the phenotype of the Cdr1 mutant can be clearly seen but not the Cds phenotypes. At 5 $\mu$M Cd the phenotypes of the Cds1-3 putative mutants can be observed. Note that on plates, slightly higher added Cd concentrations are needed than in liquid culture to achieve Cd toxicity.

Several experiments were necessary to ensure that these plasmids contain bonafide mutations in LCT1 that alter metal specificity. Initially plasmids from colonies indicating putative mutations were isolated and yeast were retransformed with selected plasmids to determine whether the phenotype (Cd-sensitivity) is stable after retransformation of yeast lines and parallel controls. Further controls were needed to ensure that mutations of interest lie in the LCT1 coding sequence and not in the plasmid DNA. Therefore the remaining full length putative mutant inserts were excised from the hydroxylamine-exposed plasmid and resubcloned into a non-mutagenized plasmid and retransformed into yeast. These controls led to the resulting putative Cd mutants isolated to date (Cdr1,Cds1-3).

The above results summarized indicate that LCT1 encodes a protein that mediates significant increases in heavy metal uptake across the plasma membrane. The gene is thus useful in enhancing heavy metal uptake into transgenic plant cells.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. An isolated nucleic acid molecule comprising at least about 100 nucleotides of an LCT1 polynucleotide sequence, which modulates metal uptake in a plant, wherein the polynucleotide sequence specifically hybridizes to SEQ ID NO: 1 under stringent conditions, wherein the stringent conditions comprise at least one wash in 0.2× SSC at a temperature of at least about 50° C. for about 20 minutes.

2. The isolated nucleic acid molecule of claim 1; wherein the LCT1 polynucleotide is between about 100 nucleotides and about 2200 nucleotides in length.

3. The isolated nucleic acid molecule of claim 1, wherein the LCT1 polynucleotide has a nucleotide sequence as shown in SEQ ID NO: 1.

4. The isolated nucleic acid molecule of claim 1, wherein the LCT1 polypeptide has an amino acid sequence as shown in SEQ ID NO: 2.

5. The isolated nucleic acid molecule of claim 1, further comprising a plant promoter operably linked to the LCT1 polynucleotide.

6. The isolated nucleic acid molecule of claim 5, wherein the plant promoter is a tissue-specific promoter.

7. The isolated nucleic acid molecule of claim 6, wherein the promoter is a root specific promoter.

8. The isolated nucleic acid of claim 5, wherein the LCT1 polynucleotide is linked to the promoter in an antisense orientation.

9. An isolated nucleic acid molecule comprising an LCT1 polynucleotide sequence, which modulates metal uptake in a plant, wherein the polynucleotide sequence encodes LCT1 polypeptide comprising a sequence as shown in SEQ ID NO:2.

10. A transgenic plant comprising an expression cassette containing a plant promoter operably linked to a heterologous LCT1 polynucleotide of claim 1.

11. The transgenic plant of claim 10, wherein the heterologous LCT1 polynucleotide encodes an LCT1 polypeptide.

12. The transgenic plant of claim 11, wherein the LCT1 polypeptide is SEQ ID NO:2.

13. The transgenic plant of claim 10, wherein the heterologous LCT1 polynucleotide is linked to the promoter in an antisense orientation.

14. The transgenic plant of claim 10, wherein the plant promoter is a tissue specific promoter.

15. The transgenic plant of claim 14, wherein the promoter is a root specific promoter.

16. The transgenic plant of claim 14, wherein the LCT1 gene is as shown in SEQ ID NO:1.

17. The transgenic plant of claim 10, which is a member of the genus Brassica.

18. A method of modulating metal uptake in a plant, the method comprising introducing into the plant an expression cassette containing a plant promoter operable linked to a heterologous LCT1 polynucleotide of claim 1.

19. The method of claim 18, wherein the heterologous LCT1 polynucleotide encodes an LCT 1 polypeptide.

20. The method of claim 19, wherein the LCT1 polypeptide has an amino acid sequence as shown in SEQ ID NO: 2.

21. The method of claim 18, wherein the heterologous LCT1 polynucleotide is linked to the promoter in an antisense orientation.

22. The method of claim 18, wherein the heterologous LCT1 polynucleotide is SEQ ID NO: 1.

23. The method of claim 18, wherein the plant promoter is a tissue specific promoter.

24. The method of claim 22, wherein the promoter is a root specific promoter.

25. The method of claim 18, wherein the plant is a member of the genus Brassica.

26. The method of claim 18, wherein the expression cassette is introduced into the plant through a sexual cross.

27. The method of claim 18, wherein the metal is a heavy metal.

28. The method of claim 18, wherein the metal is an alkali metal.

29. The method of claim 18, wherein the metal is calcium.

* * * * *